United States Patent
Miyaki et al.

(10) Patent No.: US 6,786,870 B2
(45) Date of Patent: Sep. 7, 2004

(54) DEVICE FOR EXAMINING A SUBJECT CAPABLE OF MARKING A BOUNDARY RANGE FOR INSERTION/RETRACTION OF AN INSERTION/RETRACTION MEMBER THAT IS INSERTED IN AND RETRACTED FROM THE SUBJECT

(75) Inventors: Hironaka Miyaki, Hachioji (JP); Tsutomu Urakawa, Hachioji (JP); Hiroshi Hattori, Fuchu (JP); Tatsuo Kaimai, Hachioji (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 10/277,001

(22) Filed: Oct. 21, 2002

(65) Prior Publication Data

US 2003/0078502 A1 Apr. 24, 2003

(30) Foreign Application Priority Data

Oct. 23, 2001 (JP) ........................................ 2001-325433

(51) Int. Cl.$^7$ ................................................. A61B 8/14
(52) U.S. Cl. ........................................ 600/461; 600/443
(58) Field of Search ............................... 600/437, 439, 600/443, 447, 454, 901

(56) References Cited

U.S. PATENT DOCUMENTS

| 4,346,717 A | * | 8/1982 | Haerten ................... 600/461 |
| 4,567,896 A | * | 2/1986 | Barnea et al. ............. 600/461 |
| 4,671,292 A | * | 6/1987 | Matzuk .................... 600/461 |
| 5,967,985 A | * | 10/1999 | Hayakawa ................. 600/440 |
| 6,063,031 A | * | 5/2000 | Cundari et al. ............ 600/439 |
| 6,221,016 B1 | * | 4/2001 | Hayakawa ................. 600/443 |
| 6,616,610 B2 | * | 9/2003 | Steininger et al. ......... 600/443 |
| 6,733,458 B1 | * | 5/2004 | Steins et al. .............. 600/461 |

FOREIGN PATENT DOCUMENTS

| JP | 3-173542 | 7/1991 |
| JP | 5-176922 | 7/1993 |
| JP | 8-229042 | 9/1996 |
| JP | 8-299344 | 11/1996 |
| JP | 9-122067 | 5/1997 |
| JP | 9-271472 | 10/1997 |

\* cited by examiner

*Primary Examiner*—Francis J. Jaworski
(74) *Attorney, Agent, or Firm*—Scully, Scott Murphy & Presser

(57) ABSTRACT

An ultrasound diagnostic device comprises an ultrasound endoscope, an ultrasound diagnostic signal processing device and a monitor and is arranged to obtain an ultrasound diagnostic image by performing transmission/reception of ultrasound signals with respect to a detection subject within a body cavity. The ultrasound endoscope comprises an insertion section inserted into a body cavity, an operating section and a connecting cord. A biopsy needle insertion/retraction section is employed for forward or backward insertion/retraction of a biopsy needle. The subject may be pierced by the needle tip of a biopsy needle that protrudes from a biopsy needle protrusion port at the tip of an insertion section of the ultrasound endoscope which has been inserted. The monitor displays the biopsy needle in the ultrasound diagnostic image. The ultrasound diagnostic signal processing device is constituted as superimposition means that superimposes a boundary of the advance of the piercing direction of the biopsy needle on the display of the ultrasound diagnostic image by the monitor.

18 Claims, 8 Drawing Sheets

DEVICE FOR EXAMINING A SUBJECT CAPABLE OF MARKING A BOUNDARY RANGE FOR INSERTION/RETRACTION OF AN INSERTION/RETRACTION MEMBER THAT IS INSERTED IN AND RETRACTED FROM THE SUBJECT

This application claims benefit of Japanese Application number 2001-325433 filed in Japan on Oct. 23, 2001, the contents of which are incorporated by this reference.

BACKGROUND OF THE INVENTION

1. Field of the Invention

The present invention relates to an ultrasound diagnostic device capable of obtaining an ultrasound diagnostic image by performing transmission/reception of ultrasound signals with respect to a subject in a body cavity and piercing the subject with a biopsy needle.

2. Description of the Related Art

Conventionally, in the field of medical treatment, use is made of ultrasound diagnostic devices for observation of tissues or blood flow within the body. A typical ultrasound diagnostic device chiefly comprises an ultrasound probe that transmits and receives ultrasound in respect of a part to be examined within the body and the main ultrasound device unit that is connected with the probe. Also, in such an ultrasound diagnostic device, when extracting body fluids or cells of a subject constituted by a part to be observed, a biopsy needle is employed to pierce the subject. Typically the biopsy needle is mounted on an adaptor which is freely detachably mounted on the probe. Some of such devices comprising a biopsy needle display a biopsy guide indicating the direction of insertion of the biopsy needle with respect to the desired part to be observed on a monitor screen when performing piercing whilst conducting observation of for example a B mode image.

Such prior art ultrasound diagnostic devices that display a biopsy guide are disclosed in Japanese Laid-open Patent Application No. H3-173542 or Japanese Laid-open Patent Application No. H5-176922.

In the ultrasound diagnostic device described in Japanese Laid-open Patent Application No. H3-173542, it is required that the operator should specify with visual observation the direction of insertion of the biopsy needle, using the guide groove provided in the piercing adaptor.

Also, in the ultrasound diagnostic device described in Japanese Laid-open Patent Application No. H5-176922, the allowable error of the direction in which the biopsy needle is to be inserted is displayed by two lines when the part where biopsy is to be performed is specified. The operator can easily perform biopsy when the biopsy needle is inserted arranged in a direction coincident with the set biopsy guide. However, in regard to this invention also, it is required that the operator should specify by visual observation the direction of insertion of the biopsy needle.

Consequently, in the case of both Japanese Laid-open Patent Application No. H3-173542 and Japanese Laid-open Patent Application No. H5-176922, it is an inevitable requirement that the probe should be an external ultrasound probe, since the operator must be able to specify the direction of insertion of the biopsy needle by visual observation. Thus, when, as in the case of an ultrasound endoscope, the direction in which the biopsy needle exits after insertion into a cavity of the body is variable, the operator was not able to specify by visual observation the direction of insertion of the biopsy needle.

In other words, the inventions of the ultrasound diagnostic devices described in Japanese Laid-open Patent Application No. H3-173542 and Japanese Laid-open Patent Application No. H5-176922 could not be applied to an ultrasound endoscope.

Techniques which are applicable to ultrasound endoscopes for displaying by drawings or symbols the position of a biopsy needle or the direction of insertion of a biopsy needle in an ultrasound diagnostic image are disclosed in Japanese Laid-open Patent Application No. H8-299344, Japanese Laid-open Patent Application No. H8-229042 and Japanese Laid-open Patent Application No. H9-271472.

Japanese Laid-open Patent Application No. H8-299344 discloses an ultrasound diagnostic device wherein the direction of display of the biopsy guide is made to coincide with the angle of insertion of the biopsy needle.

Japanese Laid-open Patent Application No. H8-229042 and Japanese Laid-open Patent Application No. H9-271472 disclose a technique in which the position of the tip of the biopsy needle is detected and displayed on an ultrasound tomogram.

SUMMARY OF THE INVENTION

A device for examining a subject according to the present invention comprises an image capture section capable of acquiring an image of a subject, an insertion/retraction member having a desired positional relationship with the image capture section and capable of being freely inserted/retracted with respect to the subject, an image generating section that generates an image comprising an image of the subject acquired by the image capture section and an image of the insertion/retraction member, and a boundary position superimposition section that superimposes an insertion/retraction boundary marker indicating the position of an insertion/retraction boundary of the insertion/retraction member in the image generated by the image generating section.

Other features and advantages of the present invention will become fully apparent from the following description.

BRIEF DESCRIPTION OF THE DRAWINGS

FIG. 1 to FIG. 6 relate to a first embodiment of the present invention.

FIG. 7 and FIG. 8 relate to a second embodiment of the present invention.

FIG. 9 to FIG. 11 relate to a third embodiment of the present invention.

FIGS. 13 and 14 relate to a fifth embodiment of the present invention.

DESCRIPTION OF THE PREFERRED EMBODIMENTS

Embodiments of the present invention are described below with reference to the drawings.
(First Embodiment)

First of all, the overall construction of an ultrasound diagnostic device will be described using FIG. 1.

Figure 1:
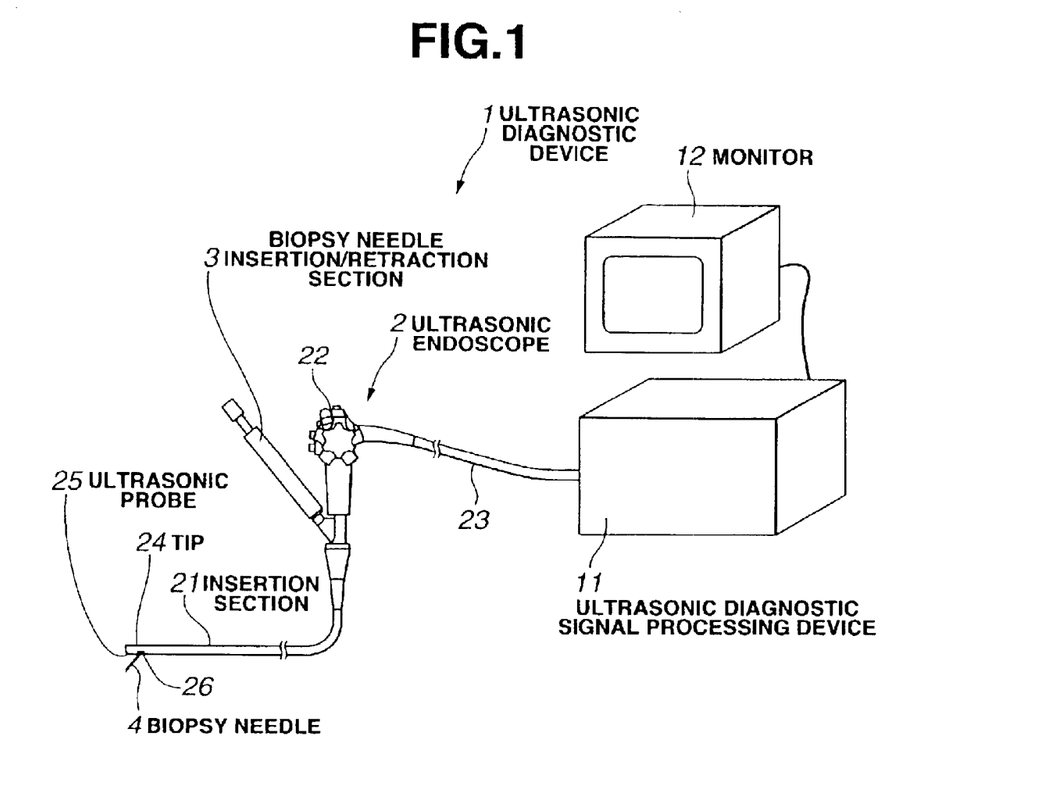
FIG. 1 is a diagram illustrating the overall construction of an ultrasound diagnostic device.

As shown in FIG. 1, an ultrasound diagnostic device 1 comprises an ultrasound endoscope 2, an ultrasound diagnostic signal processing device 11 and a monitor 12 and is arranged so as to be able to obtain an ultrasound diagnostic image by performing transmission/reception of ultrasound signals with respect to an intracavitary subject.

The ultrasound endoscope 2 comprises an insertion section 21 inserted into the body cavity, an operating section 22 and a connecting cord 23.

The ultrasound endoscope 2 comprises an ultrasound probe 25 and a biopsy needle protrusion port 26 at a tip 24 of the insertion section 21.

The ultrasound endoscope 2 is connected with the ultrasound diagnostic signal processing device 11 and performs transmission/reception of ultrasound signals with respect to the body by means of the ultrasound probe 25.

The ultrasound diagnostic signal processing device 11 controls the ultrasound probe 25 of the ultrasound endoscope 2 and processes the signals obtained from the ultrasound probe 25, and generates an ultrasound diagnostic image by known techniques and displays this on the monitor 12.

A biopsy needle insertion/retraction section 3 is mounted on the operating section 22 of the ultrasound endoscope 2. A biopsy needle insertion/retraction section 3 is employed to insert/retract a biopsy needle 4, which is a medical instrument, forward and backward. The biopsy needle 4 is inserted from the biopsy needle insertion/retraction section 3 through the insertion section 21 of the ultrasound endoscope 2 so that the tip of the needle protrudes from the biopsy needle protrusion port 26 of the tip 24 of the insertion section 21 and so can pierce the aforesaid subject.

The monitor 12 displays an image corresponding to the ultrasound diagnostic image that is output from the ultrasound diagnostic signal processing device 11. The ultrasound diagnostic signal processing device 11 has a function whereby to superimpose the insertion boundaries of the piercing direction of the biopsy needle 4 on the display of the monitor 12.

Next, the tip 24 of the ultrasound endoscope 2 will be described in detail using FIG. 2.

The ultrasound probe 25 and biopsy needle protrusion port 26 are provided at the tip 24 of the ultrasound endoscope 2.

An angle adjuster 27 for adjusting the angle with which the biopsy needle 4 protrudes from the tip of the ultrasound endoscope 2 is provided in the interior of the biopsy needle protrusion port 26. In this case, the angle adjuster 27 is mounted in a condition in which it is rotatable by a rotary shaft 28 in a direction perpendicular to the longitudinal direction of the insertion section 21. Furthermore, the angle adjuster 27 is made capable of rotating between one and the other adjustment boundary positions by operation of the operating section 22 shown in FIG. 1.

Figure 2:
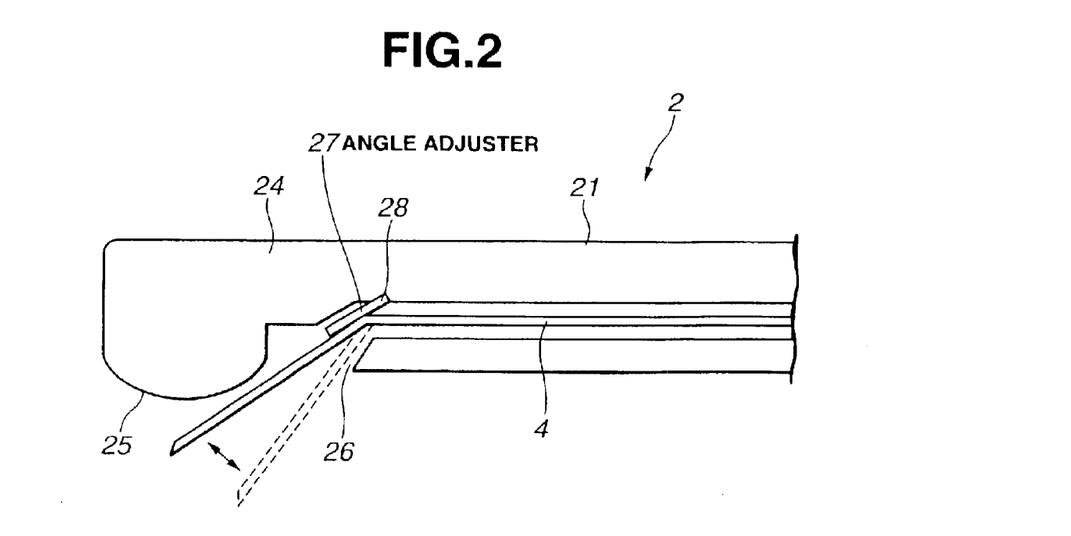
FIG. 2 is a sectional view of the tip of an ultrasound endoscope.

FIG. 2 shows with a solid line the case where the biopsy needle 4 in the one adjustment boundary position of the angle adjuster 27 protrudes from the tip 24 of the ultrasound endoscope 2. The broken line shows the position when the biopsy needle 4 is in the other adjustment boundary position.

In the one adjustment boundary position, the angle adjuster 27 and biopsy needle 4 are in the condition of smallest angle with respect to the longitudinal direction of the insertion section 21. The angle with which the biopsy needle 4 protrudes from the tip 24 of the ultrasound endoscope 2 depends on the type of ultrasound endoscope 2 and so the angle is a known quantity.

Figure 3:
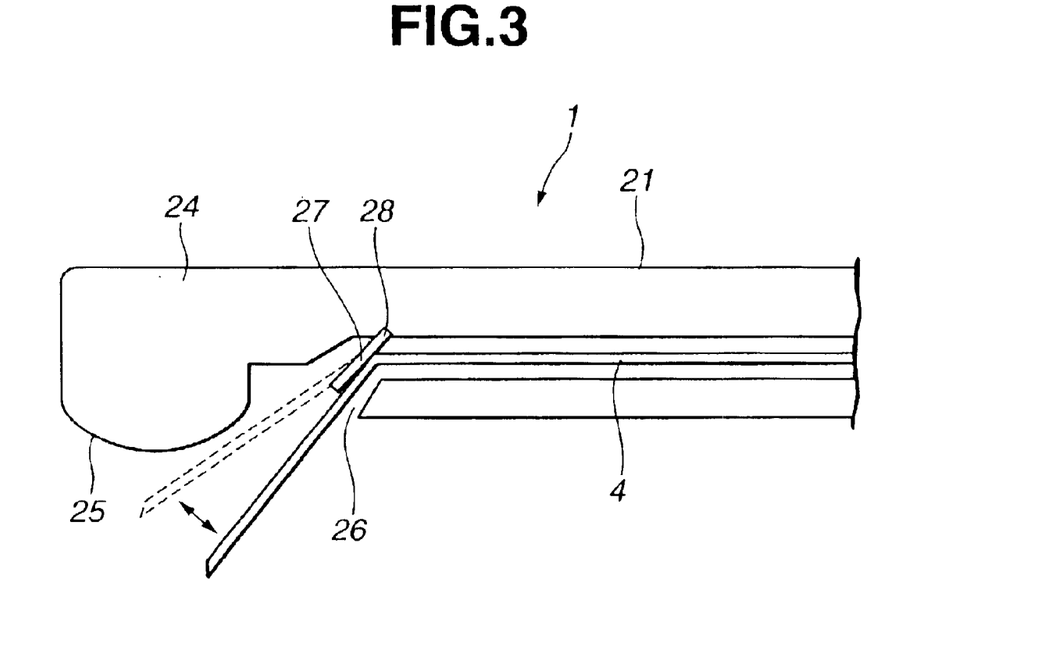
FIG. 3 is a diagram illustrating the limits of adjustment of a tip angle adjuster of the ultrasound endoscope.

In FIG. 3, the case where the biopsy needle 4 protrudes from the tip 24 of the ultrasound endoscope 2 in the aforesaid other adjustment boundary position of the angle adjuster 27 is indicated by a solid line. The broken line indicates the position of the biopsy needle 4 at the one adjustment boundary position. In case that the angle adjuster 27 and the biopsy needle 4 are positioned in the other adjustment boundary position, the angle with respect to the longitudinal direction of the insertion section 21 is largest. In this case also, the angle with which the biopsy needle 4 protrudes from the tip 24 of the ultrasound endoscope 2 is a known quantity.

With this construction, the angle adjuster 27 is provided within the aforesaid insertion section 21 and has a function whereby to alter the direction of piercing of the aforesaid biopsy needle 4 by movement thereof.

The ultrasound wave diagnostic signal processing device 11 superimposes the movement range of this angle adjuster 27 on the ultrasound diagnostic image of the monitor 12.

Figure 4:
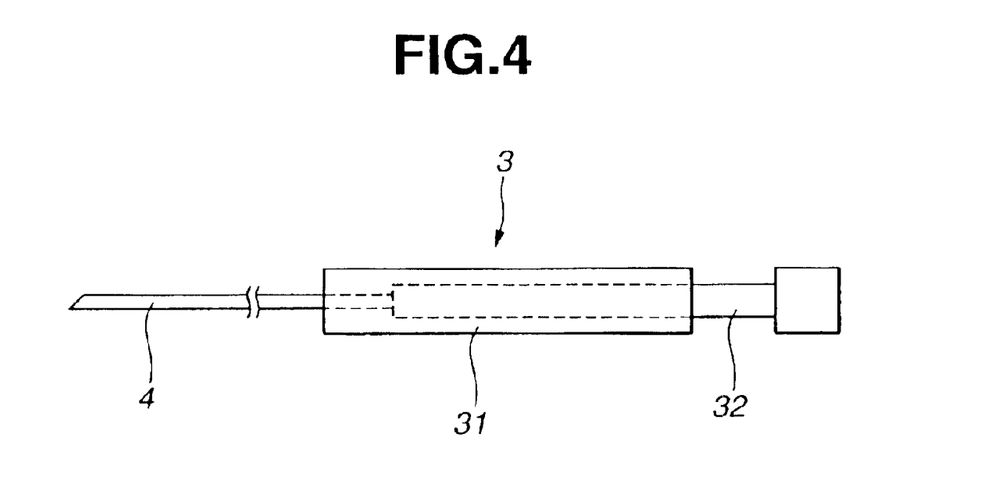
FIG. 4 is a side view illustrating an example of the construction of a biopsy needle and biopsy needle insertion/retraction section.

FIG. 4 illustrates an example of the construction of the biopsy needle insertion/retraction section 3 and the biopsy needle 4.

The biopsy needle insertion/retraction section 3 comprises a biopsy needle insertion/retraction section casing 31 and a piston 32. The biopsy needle 4 is mounted on the piston 32 and is inserted/retracted with forward/backward movement of the piston 32.

In the condition shown in FIG. 1 in which the biopsy needle insertion/retraction section 3 is mounted on the ultrasound endoscope 2, the biopsy needle 4 protrudes from the tip 24 of the ultrasound endoscope 2 when the operator pushes the piston 32.

Although an example of the simplest construction of the biopsy needle insertion/retraction section 3 is illustrated in FIG. 4, the biopsy needle insertion/retraction section 3 is not restricted to a biopsy needle insertion/retraction section of the construction shown in FIG. 4. It would be possible to employ a biopsy needle insertion/retraction section provided with a stop for preventing pushing the end of the piston beyond a pre-set stroke, or a biopsy needle insertion/attraction section wherein the piston is advanced by a pre-set stroke by operation of a button.

(Operation)

Figure 5:
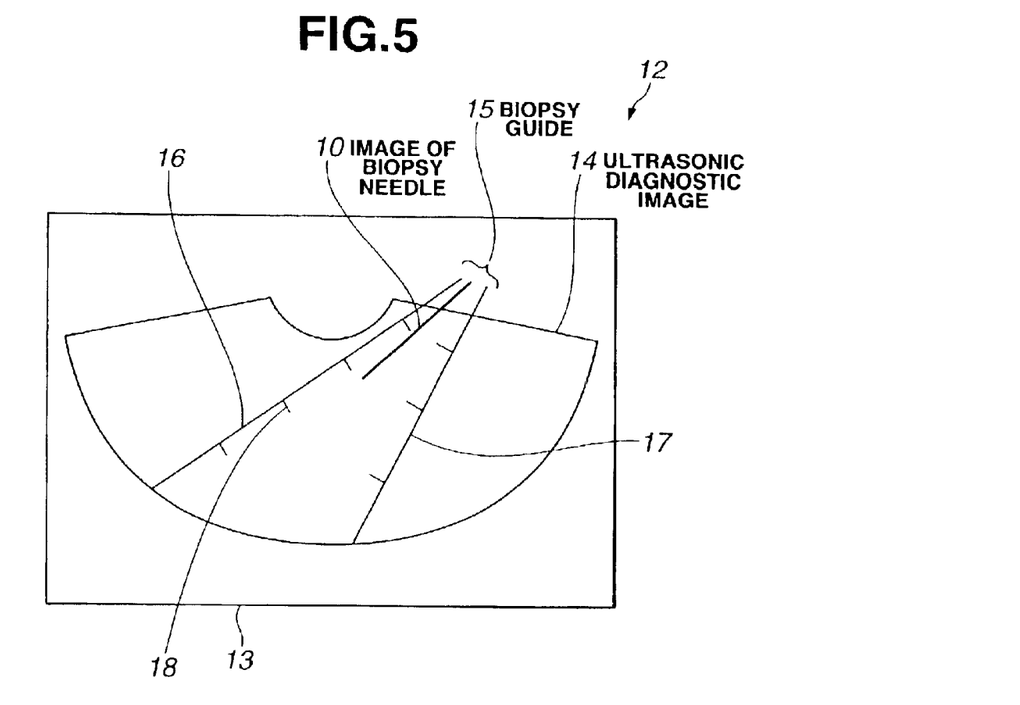
FIG. 5 is a diagram illustrating an example of a first display of an image output to a monitor by the ultrasound diagnostic device.

FIG. 5 shows an example of the display of an image which is output to the monitor 12 by the ultrasound diagnostic signal processing device 11.

In FIG. 5, a sector-shaped ultrasound diagnostic image 14 is displayed on the screen 13 of the monitor 12. The biopsy needle image 10 is an ultrasound image corresponding to the biopsy needle 4 displayed on the ultrasound diagnostic image 14 and is displayed as a high-brightness echo of linear shape. Display or non-display of the biopsy guide 15 can be selected as desired; this display is superimposed on the ultrasound diagnostic image 14 when display is selected by a changeover switch (not shown) of the ultrasound diagnostic signal processing device 11. The biopsy guide 15 comprises biopsy guidelines 16 and 17. When the angle adjuster 27 of the ultrasound endoscope 2 is in the one adjustment boundary position shown in FIG. 2, the biopsy guideline 16 coincides with the direction of the biopsy needle image 10 displayed on the ultrasound diagnostic image 14. As described above, if the type of the ultrasound endoscope 2 is determined, the angle with which the biopsy needle 4 protrudes when this angle adjuster 27 is in the one adjustment boundary position is a known quantity, so the biopsy guideline 16 may be displayed in a direction coinciding with this direction. In the ultrasound diagnostic signal processing device 11, means for specifying the type of the ultrasound endoscope 2 connected thereto can easily be implemented using known techniques. The biopsy guideline 17 likewise coincides with the direction in which the biopsy needle image 10 is displayed on the ultrasound diagnostic image 14 when the angle adjuster 27 of the ultrasound endoscope 2 shown in FIG. 3 is in the other adjustment boundary position. The biopsy needle 10 must therefore be displayed within the area defined by the biopsy guidelines 16 and 17.

Also, since the piston 32 of biopsy needle insertion/retraction section 3 shown in FIG. 4 is chiefly operated manually by the operator, graduations 18 providing a scale of the length with which how deep the piston 32 should be pushed in are displayed on the biopsy guidelines 16 and 17.

Figure 6:
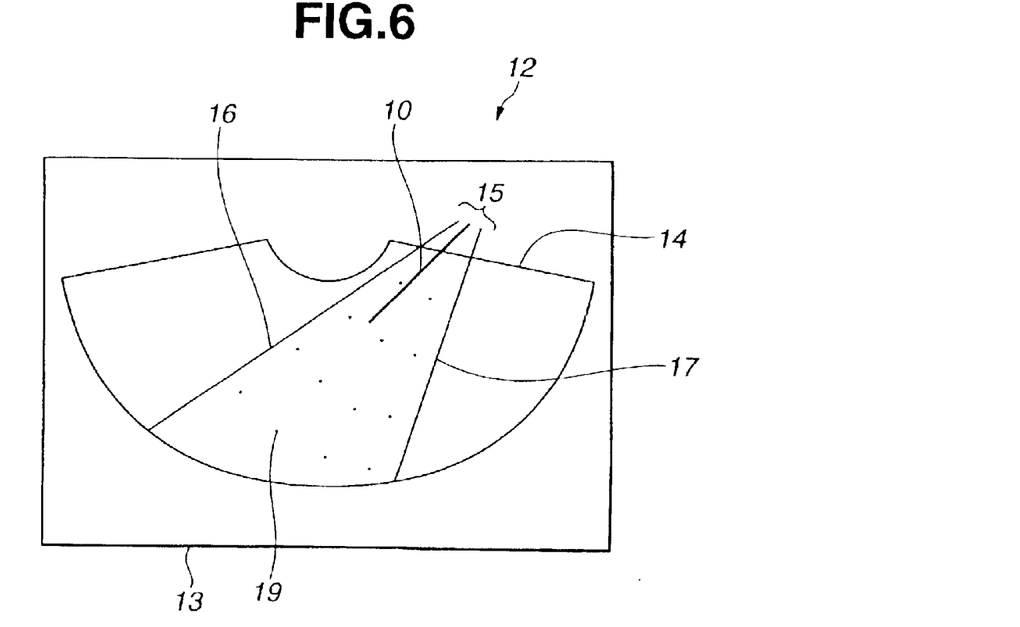
FIG. 6 is a diagram illustrating a second example of a display of an image output to a monitor by the ultrasound diagnostic device.

Also, instead of the display of graduations 18 or in combination therewith, dot marks 19 may be displayed at prescribed intervals within the range defined by biopsy guidelines 16 and 17 as shown in FIG. 6. By displaying the dot marks 19, the length of the biopsy needle image 10 can easily be recognized by the operator even when the biopsy needle image 10 is remote from the biopsy guidelines 16 and 17.

(Effects)

Thus, with the first embodiment, biopsy can be performed confidently, since the operator can recognize the range through which the biopsy needle has advanced by using the display of the biopsy guide 15, even in cases where the direction of the biopsy needle cannot be directly visually ascertained by the operator, such as in the case of an ultrasound endoscope.

Furthermore, with the first embodiment, by displaying the dot marks 19 as shown in FIG. 6 or graduations 18 as shown in FIG. 5, the length of advance can be ascertained, wherever the diagnostic needle has advanced to within the biopsy guide range.

(Second Embodiment)

Figure 7:
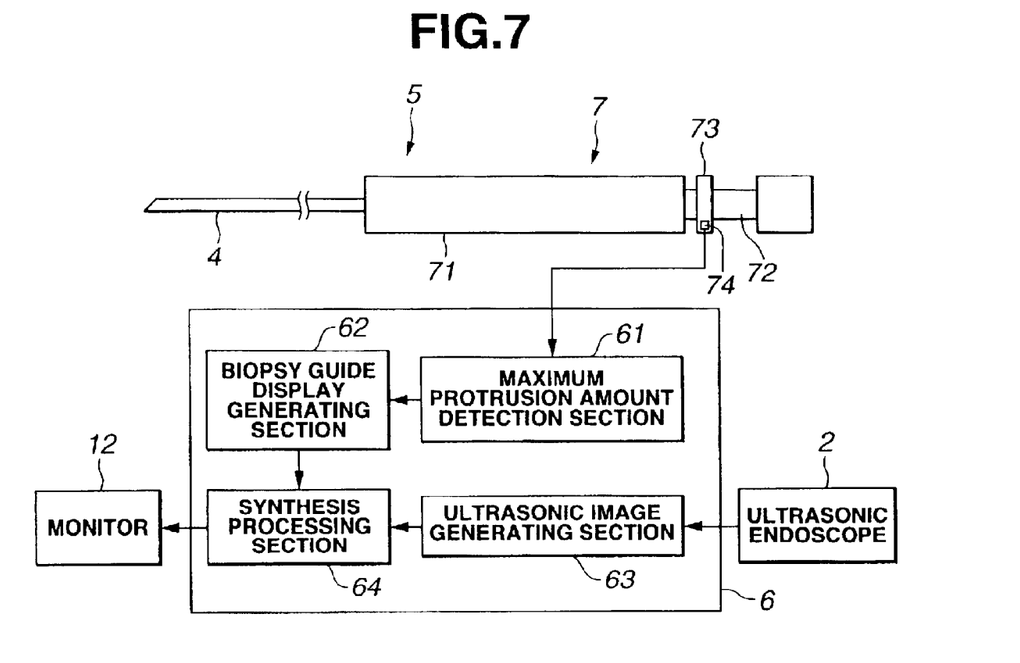
FIG. 7 is a block diagram illustrating the overall construction of an ultrasound diagnostic device.
Figure 8:
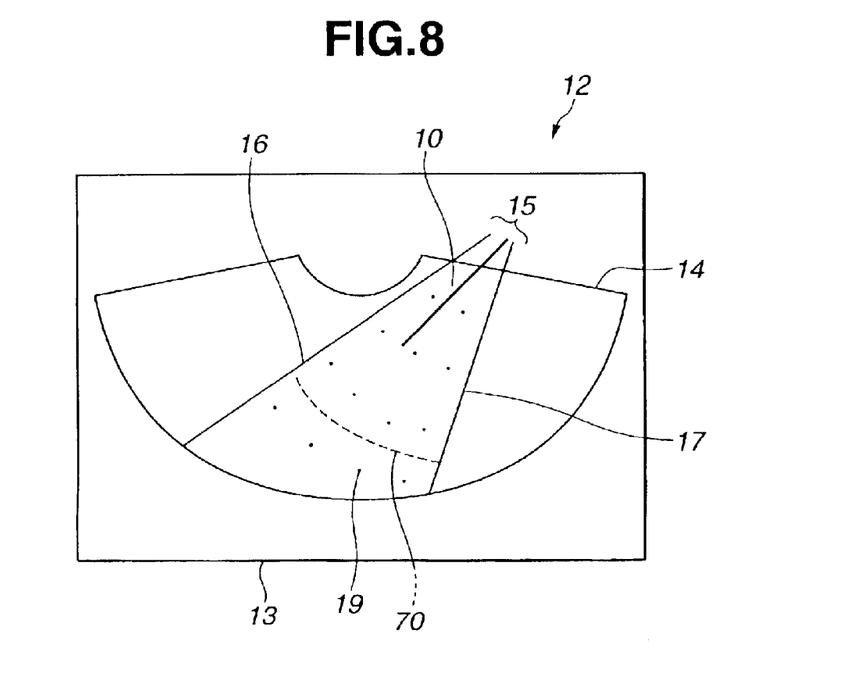
FIG. 8 is a diagram illustrating an example of a display of an image output to a monitor by the ultrasound diagnostic device.

In the description of FIG. 7 and FIG. 8, structural elements which are the same as in the first embodiment shown in FIG. 1 to FIG. 6 are given the same reference symbols and further description thereof is omitted.

(Constitution)

In FIG. 7, an ultrasound diagnostic device 5 comprises the ultrasound endoscope 2, ultrasound diagnostic signal processing device 6, biopsy needle insertion/retraction section 7 and monitor 12.

An example is illustrated in which the ultrasound diagnostic signal processing device 6 can be combined with a biopsy insertion/retraction section 7 having a mechanism for detecting the maximum amount of protrusion of the biopsy needle 4.

The biopsy diagnostic signal processing device 6 comprises a maximum protrusion amount detection section 61, a biopsy guide display generating section 62, an ultrasound image generating section 63 and a synthesis processing section 64.

The biopsy needle insertion/retraction section 7 comprises a biopsy needle insertion/retraction section casing 71, a piston 72 and a stop 73. The biopsy needle 4 is mounted on the piston 72.

The stop 73 is mounted at the proximal end of the biopsy needle insertion/retraction casing 71 in a condition in which its position can be adjusted. The stop 73 serves to prevent the piston 72 being pushed in by more than stroke set by position adjustment in advance.

A sensor 74 is incorporated in the stop 73. The sensor 74 outputs data corresponding to the fixed position of the stop 73 to the ultrasound diagnostic signal processing device 6.

The sensor 74 is constituted by for example a sensor comprising an encoder that converts the amount of movement in the forward/backward direction of the stop 73 into the number of pulses to output, or a sensor wherein the resistance value of a variable resistance changes with forward/backward movement of the stop 73 and is converted into the amount of movement by detecting the voltage difference across the two ends of this variable resistance, or a magnetic sensor wherein the distance from the end of the piston 72 is measured by detecting the strength of magnetism formed by a magnet embedded in one end of the piston 72.

The data that is output by the sensor 74 is input to the maximum protrusion amount detection section 61 within the ultrasound diagnostic signal processing device 6. The maximum protrusion amount detection section 61 detects the set position i.e. the maximum protrusion amount of the stop 73 using the data from the sensor 74.

The data of the detection result of the maximum protrusion amount detection section 61 is sent to the biopsy guide display generating section 62. Based on the data from the maximum protrusion amount detection section 61, the biopsy guide display generating section 62 generates an image of the biopsy guide with the utmost position reached by the biopsy needle, to be described below, attached thereto.

The ultrasound image generating section 63 processes the signal obtained from the ultrasound endoscope 2, generates an ultrasound diagnostic image by known techniques and outputs this to the synthesis processing section 64.

The image of the biopsy guide with the utmost position reached by the biopsy needle attached thereto created by the biopsy guide display generating section 62 is synthesized with the ultrasound diagnostic image generated by the ultrasound image generating section 63 in the synthesis processing section 64 and displayed on the monitor 12.

(Operation)

An example of the display of a biopsy guide with the utmost position reached by the biopsy needle attached thereto is illustrated using FIG. 8.

As shown in FIG. 8, a biopsy guide 15 is displayed on an ultrasound diagnostic image 14 of a screen 13 of the monitor 12 and, in addition, the utmost position 70, constituting the aforesaid boundary of insertion in the piercing direction, that is reached by the biopsy needle is displayed. The utmost position 70 reached by the biopsy needle is displayed as an arcuate dotted line or solid line.

When the operator alters the position of the stop 73 of the biopsy needle insertion/retraction section 7, the position of the stop 73 is detected by the aforesaid construction and the utmost position 70 reached by the biopsy needle is updated by the movement interlocked with the movement of the stop 73.

(Effects)

With the second embodiment, the same benefits as in the case of the first embodiment illustrated in FIG. 1 to FIG. 6 are obtained and, even in the case of a biopsy needle 4 wherein the stop position of the biopsy needle 4 can be altered, the utmost position reached by the biopsy needle 4 can be displayed being interlocked with the stop 73 which constitutes the stop mechanism of the mechanical biopsy needle 4, so ease of the piercing operation can be improved, and the operator can perform a biopsy using the biopsy needle with confidence.

It should be noted that the biopsy guides used in the first and second embodiments are not restricted to those illustrated in FIG. 5, FIG. 6 and FIG. 8 and the solid lines could be replaced by the dotted lines or the broken lines.

(Third Embodiment)

However, when, as in the case of an ultrasound endoscope, the direction of protrusion of the biopsy needle after insertion into the body cavity can be varied, the operator cannot specify the direction of insertion of the biopsy needle by direct visual observation. There was previously no biopsy guide display in existence that displayed the direction of protrusion with respect to a biopsy needle whose direction of insertion could not be specified by the operator, as is the case in regard to an ultrasound endoscope. The operator of the ultrasound endoscope therefore previously had no means at all of knowing the direction of insertion of the biopsy needle and so could not conduct a biopsy with confidence.

The third embodiment addresses these problems.

Figure 9:
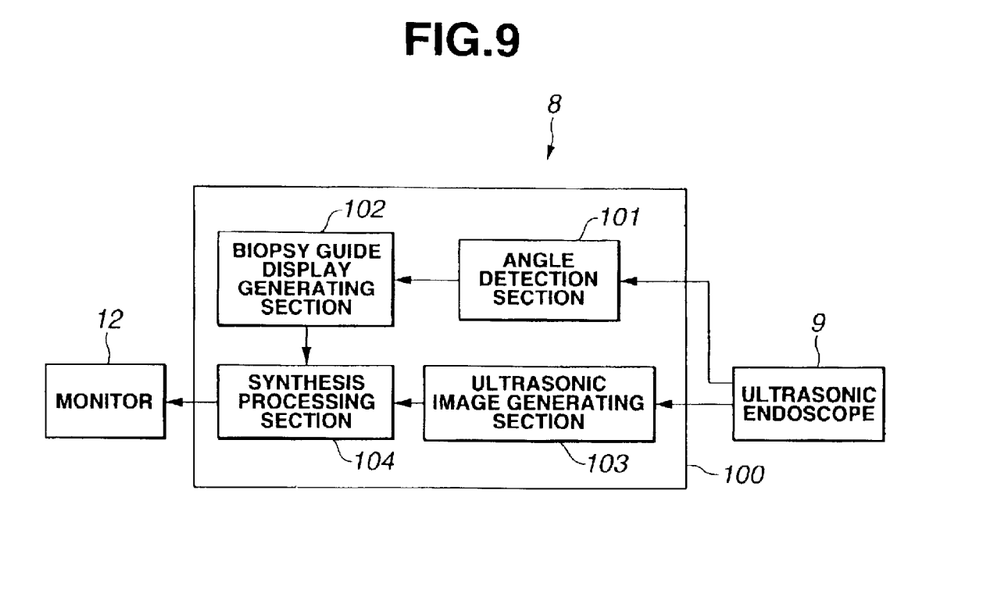
FIG. 9 is a block diagram illustrating the overall construction of an ultrasound diagnostic device.
Figure 10:
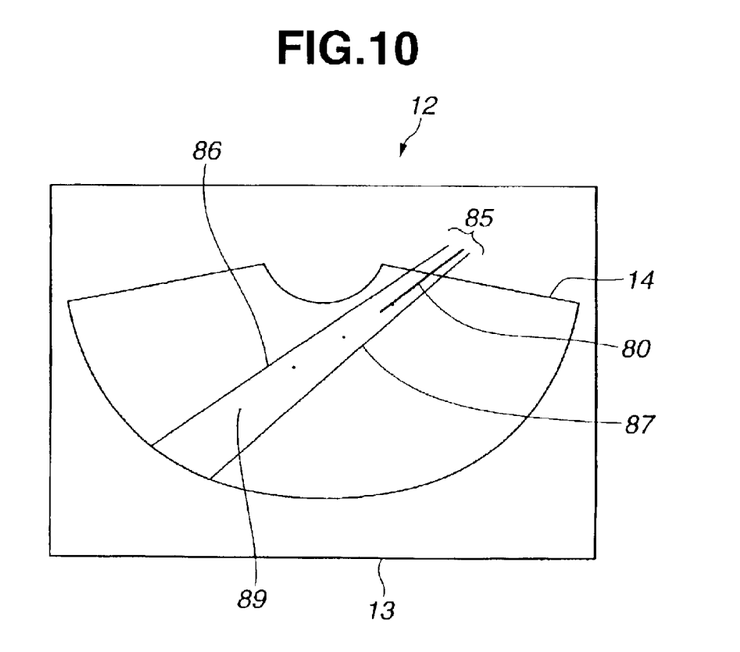
FIG. 10 is a diagram illustrating an example of a first display of an image output to a monitor by an ultrasound diagnostic device.
Figure 11:
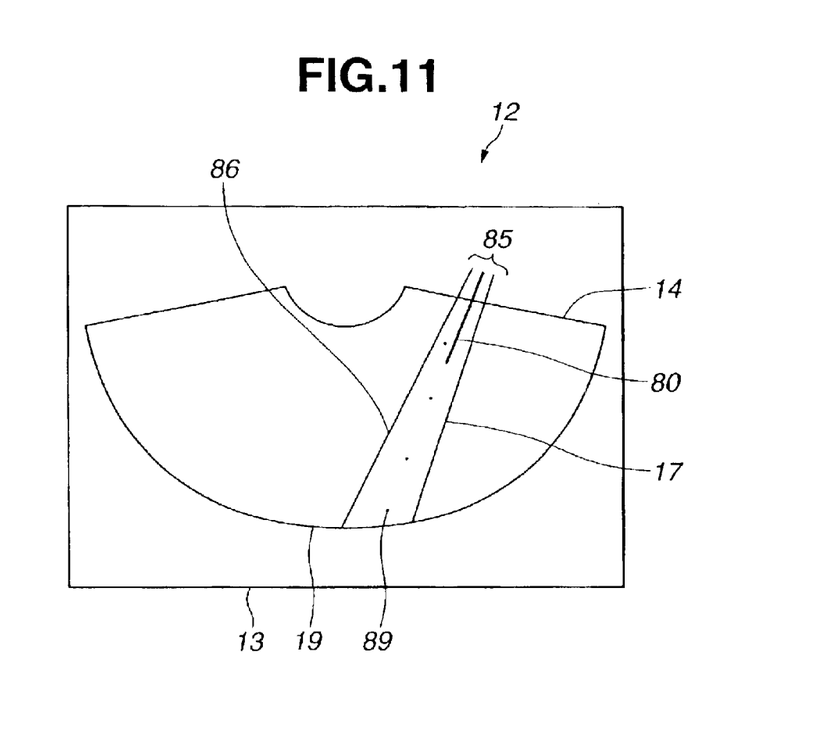
FIG. 11 is a diagram illustrating a second example of a display of an image output to a monitor by an ultrasound diagnostic device.

In the description of FIG. 9 to FIG. 11, structural elements which are the same as in the case of the first embodiment illustrated in FIG. 1 to FIG. 6 are given the same reference symbols and further description thereof is omitted. Also, portions which are not shown in FIG. 9 will be described with reference to FIG. 2 instead.

(Constitution)

In FIG. 9, an angle output section (not shown) that outputs an angle set by an angle adjuster 27 shown in FIG. 2 is built in an ultrasound endoscope 9. The angle output section is integral with or constructed separately from the angle adjuster 27 of the tip 24 of the endoscope 2 shown in FIG. 2 and is arranged to output an angle set as a resistance value change etc produced by a variable resistor, or as a pulse output produced by an encoder.

An ultrasound diagnostic signal processing device 100 comprises an angle detection section 101, a biopsy guide display generating section 102, an ultrasound image generating section 103 and a synthesis processing section 104.

The data output from the angle output section is sent to the angle detection section 101 of the ultrasound diagnostic signal processing device 100. The angle detection section 101 calculates the angle of the angle adjuster 27 using the data sent from the angle output section. The angle of the angle adjuster 27 calculated by the angle detection section 101 is sent to the biopsy guide display generating section 102. The biopsy guide display generating section 102 generates a biopsy guide, to be described.

In addition, the ultrasound echo of the ultrasound endoscope 9 is sent to the ultrasound image generating section 103 of the ultrasound diagnostic signal processing device 100. The ultrasound image generating section 103 generates an ultrasound diagnostic image using the ultrasound echo that is sent to it. The synthesis processing section 104 synthesizes a biopsy guide generated by the biopsy guide display generating section 102 with the ultrasound diagnostic, image generated by the ultrasound image generating section 103 and outputs the result to the monitor 12.

(Operation)

FIG. 10 shows an example of an image output to the monitor 12 by the ultrasound diagnostic signal processing device 100.

Since, as described previously, the ultrasound diagnostic signal processing device 100 detects the angle of the angle adjuster 27 of the ultrasound endoscope 9, a biopsy guide 85 displayed on the monitor 12 is displayed in a direction coinciding with the direction of insertion of a biopsy needle image 80.

When the operator changes the angle of the angle adjuster 27, the direction of the biopsy guide 85 changes for example as shown in FIG. 11. The separation of the biopsy guidelines 86 and 87 is determined taking into account the accuracy of the angle output section incorporated in the ultrasound endoscope 9 and the calculation error of the angle detection section 101. Typically, display is effected with a width of the order of a few times to ten times that of the biopsy needle image 80. Also, if required, dot marks 89 may be displayed with a prescribed separation.

(Effects)

As described above, with the third embodiment, since it is possible to display a biopsy guide of the direction coincident with the direction of insertion of the biopsy needle, the operator of the ultrasound endoscope, when employing a biopsy needle whose direction of insertion can be varied, can reliably ascertain the direction of insertion of the biopsy needle by means of the biopsy guide 85 displayed on the monitor 12 and can therefore conduct biopsy with confidence.

(Fourth Embodiment)

Figure 12:
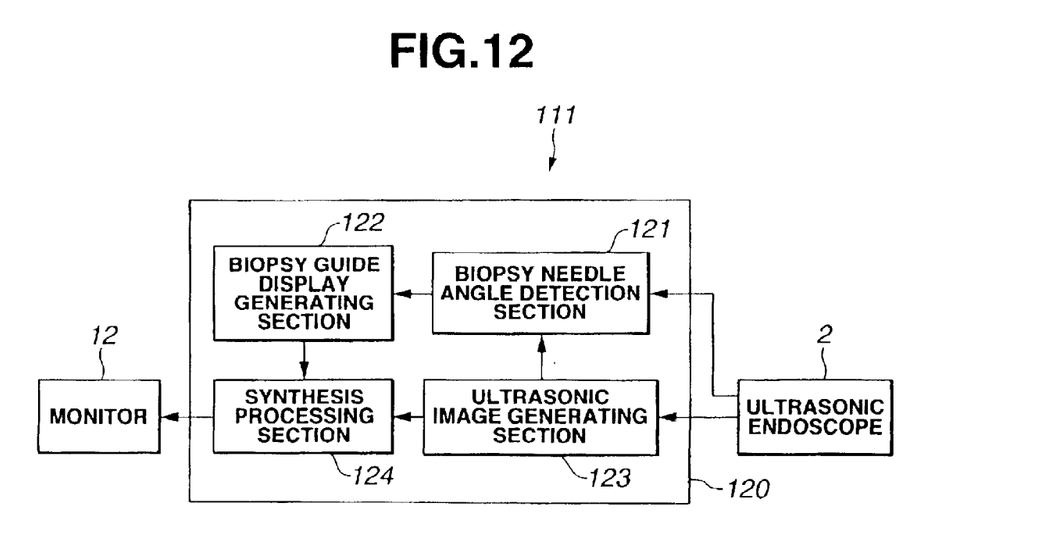
FIG. 12 is a block diagram illustrating the overall construction of an ultrasound diagnostic device according to a fourth embodiment of the present invention.

In the description of FIG. 12, structural elements which are the same as in the case of the first embodiment shown in FIG. 1 to FIG. 6 are given the same reference symbols and further description thereof is omitted.

(Constitution)

In FIG. 12, an ultrasound diagnostic device 111 is made capable of displaying a biopsy guide coincident with the direction of insertion of the biopsy needle when combined with an ultrasound endoscope 2 that does not have an angle output section that outputs the angle of the angle adjuster.

An ultrasound diagnostic signal processing device 120 comprises a biopsy needle angle detection section 121, a biopsy guide display generating section 122, an ultrasound image generating section 123 and synthesis processing section 124.

The ultrasound diagnostic signal processing device 120 generates an ultrasound diagnostic image with the ultrasound image generating section 123 using the ultrasound echoes from the ultrasound endoscope 2. The biopsy needle angle detection section 121 performs a calculation of the direction of the biopsy needle as follows, using the ultrasound diagnostic image generated by the ultrasound image generating section 123.

(Operation)

If the biopsy needle is present on the ultrasound diagnostic image, the biopsy needle is displayed as a linear high-brightness echo as the biopsy needle image 10 of FIG. 5. The biopsy needle angle detection section 121 performs detection by performing image processing to ascertain whether or not a high-brightness echo which is linear and not shorter than a prescribed length is present.

The length of the linear echo that is used by the biopsy needle angle detection section 121 as a standard for deciding whether or not a biopsy needle image is present is specified beforehand as about 1 cm, but the length of the linear echo constituting the standard for this decision can be set at the operator's discretion by using a switch, not shown, on the ultrasound diagnostic signal processing device 120.

If the biopsy needle angle detection section 121 does not detect a linear echo of at least the standard length, it decides that no biopsy needle is being displayed. The biopsy guide display generating section 122 therefore displays on the monitor 12 a biopsy guide 15 having the biopsy guidelines 16 and 17 at both ends as adjustment boundary positions of the angle of the biopsy needle as in FIG. 5 or FIG. 6. If the biopsy needle angle detection section 121 detect that a linear echo is not shorter than the standard length, it decides that the biopsy needle is present in the ultrasound diagnostic image and sends the result of calculation of its angle information to the biopsy guide display generating section 122. Regarding the method of displaying the biopsy guide on the monitor after the angle calculation information of the biopsy needle has been sent by the biopsy guide display generating section 122, this is the same as in the case of the construction of the biopsy guide display generating section 102 of the ultrasound diagnostic signal processing device 100 shown in FIG. 9. The biopsy guide displayed on the monitor 12 is therefore the same as in the case of FIG. 10 or FIG. 11.

(Effects)

With the fourth embodiment, even in cases where the ultrasound endoscope does not have an angle output section that outputs the angle of the angle adjuster, the operator can ascertain by means of the biopsy guide displayed on the monitor 12 in what direction the biopsy needle is effecting piercing and so can conduct biopsy with confidence.

(Fifth Embodiment)

The piercing ultrasound probe disclosed in Japanese Laid-open Patent Application No. H8-229042 or the position detection device of a piercing needle and ultrasound diagnostic device disclosed in Japanese Laid-open Patent Application No. H9-271472 relate to inventions in which the tip position of the biopsy needle is detected and displayed. With these devices, the tip position of the biopsy needle can be specified, but the operator must take care to avoid contacting with blood vessels and so could not perform biopsy with confidence.

The fifth embodiment addresses this problem.

Figure 13:
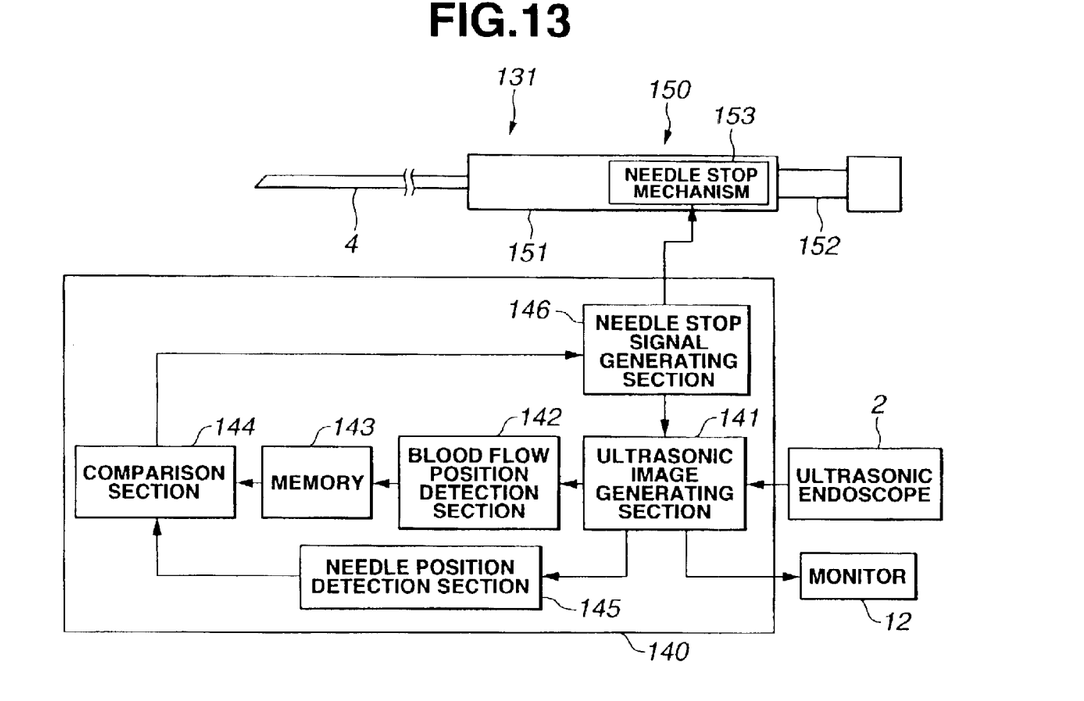
FIG. 13 is a block diagram illustrating the overall layout of an ultrasound diagnostic device.
Figure 14:
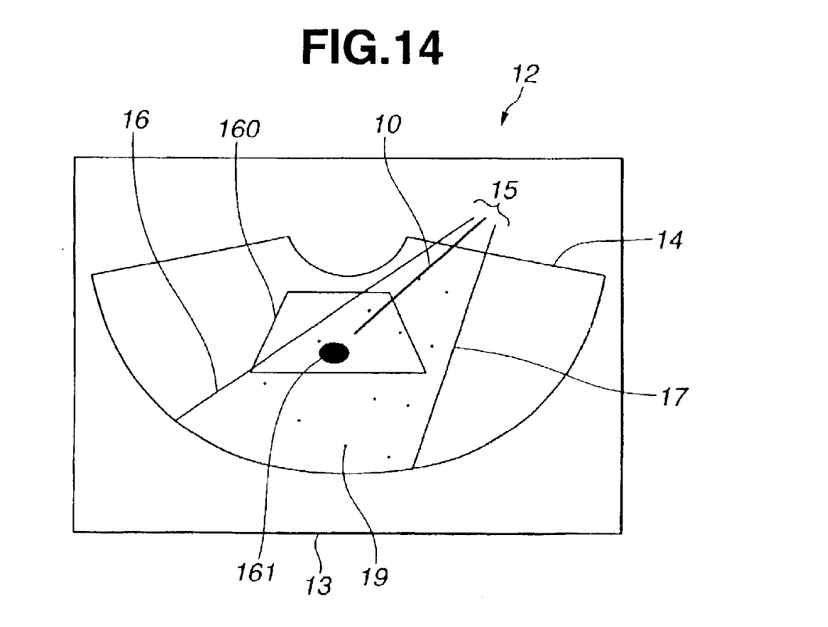
FIG. 14 is a diagram illustrating an example of a display of an image output to a monitor by an ultrasound diagnostic device.

In the description of FIG. 13 and FIG. 14, structural elements which are same as in the case of the first embodiment shown in FIG. 1 to FIG. 6 are given the same reference symbols and further description thereof is omitted.

(Constitution)

In FIG. 13, an acoustic diagnostic device 131 has a function of stopping the biopsy needle 4.

An acoustic diagnostic signal processing device 140 comprises an acoustic image generating section 141, blood flow position detection section 142, memory 143, comparison section 144, needle position detection section 145 and needle stop signal generating section 146.

A biopsy needle insertion/retraction section 150 comprises a biopsy needle insertion/retraction or section casing 151, piston 152 and needle stop mechanism 153.

The acoustic diagnostic signal processing device 140 outputs a needle stop signal from the needle stop signal generating section 146 by the method to be described. A needle stop mechanism 153 of the biopsy insertion/retraction section 150 receives a needle stop signal from the needle stop signal generating section 146. When it receives the needle stop signal, the needle stop mechanism 153 locks the piston 152 with respect to the biopsy needle insertion/retraction section casing 151 so that it cannot move further in the pushing-in direction. By locking the piston 152 by the needle stop mechanism 153, the biopsy needle insertion/retraction section 150 prevents further protrusion of the biopsy needle 4.

(Operation)

The method of generating the needle stop signal will now be described.

The ultrasound diagnostic signal processing device 140 has a Doppler function like that of an ordinary ultrasound diagnostic device and this Doppler function is turned on when the needle stop signal is generated.

When the Doppler function of the ultrasound diagnostic signal processing device 140 is turned on, the ultrasound image generating section 141 displays a Doppler cursor 160 as shown in FIG. 14 on the monitor 12, using the signal from the ultrasound endoscope 2, and when blood flow is detected a blood flow information 161 is displayed. The blood flow position detection section 142 of the ultrasound diagnostic signal processing device 140 stores the position data at which a Doppler signal is detected by the ultrasound image generating section 141 in the memory 143 and updates the position data stored in the memory 143 every time the position at which the Doppler signal was detected changes. The needle position detection section 145 detects the linear high-brightness echo that is characteristic of a biopsy needle image 10 in which the biopsy needle 4 is drawn on the ultrasound diagnostic image 14 from the ultrasound diagnostic image of the ultrasound image generating section 141 by image processing and calculates the position corresponding to the tip of the biopsy needle 4. The comparison section 144 performs a comparison of the position data of a blood clot stored in the memory 143 with the position data of the tip of the biopsy needle 4 calculated by the needle position detection section 145.

In the comparison section 144, an approach-avoidance distance constituting a criterion for the evaluation of the degree of proximity of the tip position of the biopsy needle 4 and the blood flow position is laid down; it outputs a needle stop signal to the needle stop signal generating section 146 if the tip position of the biopsy needle 4 and the blood flow position are within the approach-avoidance distance. The needle stop mechanism 153 thereby locks and stops the biopsy needle 4. In this case, the approach-avoidance distance is set beforehand at about 1 cm; it can be altered at the operator's discretion using a switch, not shown, on the ultrasound diagnostic device.

Although the biopsy guide 15 is simultaneously displayed in FIG. 14, the biopsy guide 15 is not necessarily essential and it would be possible for the ultrasound diagnostic signal processing device 140 not to have a biopsy guide display function.

(Effects)

With the fifth embodiment, if blood flow is detected, the blood flow information 161 is displayed and if the position of the tip of the biopsy needle 4 and the blood flow position are within the approach-avoidance distance, the biopsy needle 4 is stopped, so biopsy can be conducted with confidence.

(Sixth Embodiment)

(Constitution)

Figure 15:
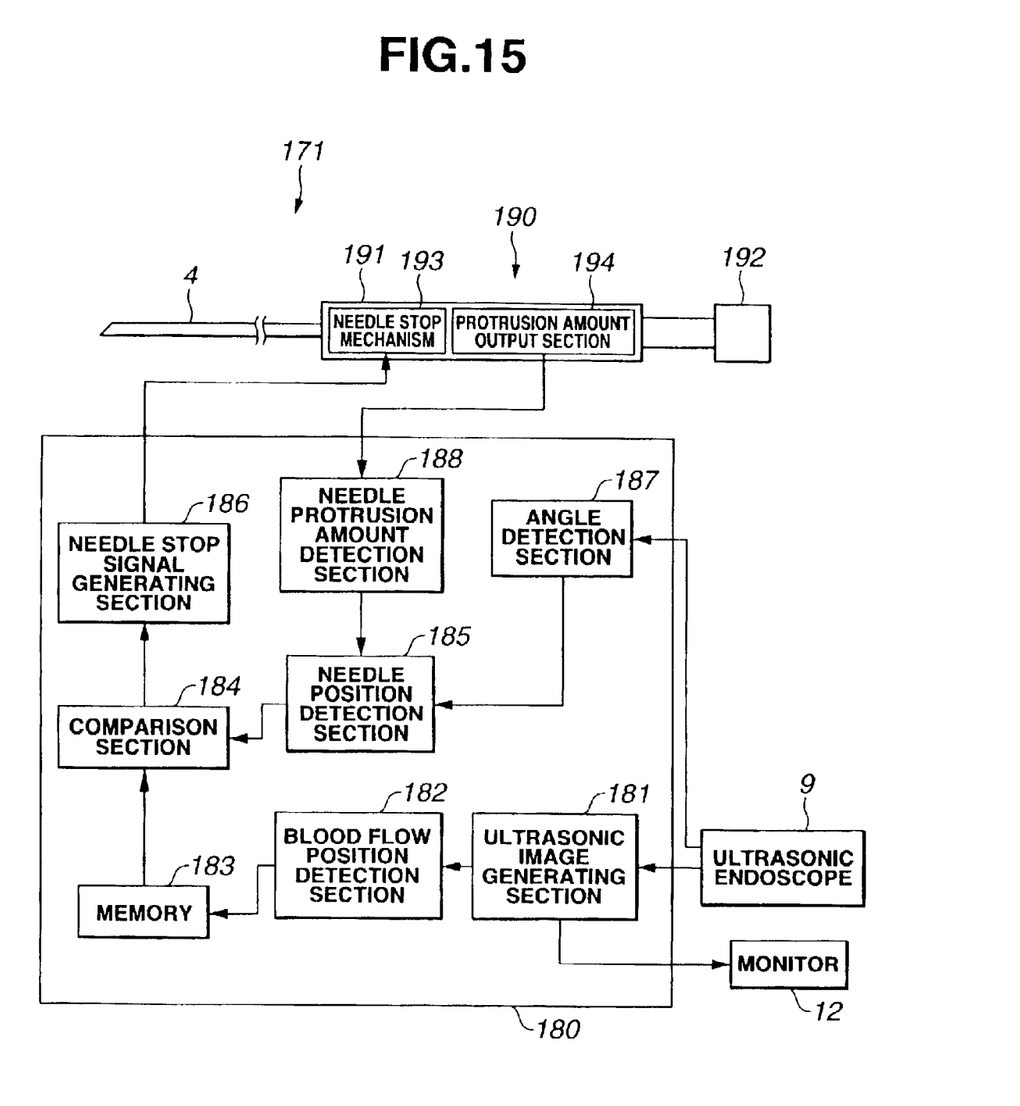
FIG. 15 is a block diagram illustrating the overall construction of an ultrasound diagnostic device according to a sixth embodiment of the present invention.

In FIG. 15, an ultrasound diagnostic device 171 illustrates an ultrasound diagnostic device having a function of stopping the biopsy needle 4 of a different construction from that of FIG. 13.

An ultrasound diagnostic signal processing device 180 comprises an ultrasound image generating section 181, a blood flow position detection section 182, a memory 183, a comparison section 184, a needle position detection section 185, a needle stop signal generating section 186, an angle detection section 187 and a needle protrusion amount detection section 188.

A biopsy needle insertion/retraction section 190 comprises a biopsy needle insertion/retraction section casing 191, piston 192, needle stop mechanism 193 and protrusion amount output section 194.

The function of the needle stop mechanism 193 is the same as that of the needle stop mechanism 153 in the biopsy needle insertion/retraction section 150 of FIG. 13. The protrusion amount output section 194 outputs data corresponding to the insertion/retraction position of the piston 192 with respect to the biopsy needle insertion/retraction section casing 191 obtained by means of a pulse output produced by an encoder, a variable resistance value produced by a variable resistor, magnetic intensity produced by a magnetic sensor or the like.

(Operation)

The angle detection mechanism produced by the combination of the ultrasound endoscope 9 and the angle detection section 187 is the same as the construction of the ultrasound diagnostic signal processing device 100 shown in FIG. 9. The needle protrusion amount detection section 188 calculates in real time the amount of protrusion of the biopsy needle 4 from the position data of the piston 192 obtained from the protrusion amount output section 194.

The needle position detection section 185 calculates the tip position of the biopsy needle 4 from the amount of protrusion of the biopsy needle 4 calculated by the needle protrusion amount detection section 188 and the angle of the angle adjuster obtained by the angle adjustment section 187. The detection of the blood flow position by the blood flow position detection section 182, storing of the blood flow position data in the memory 183 and the construction, whereby the tip position of the biopsy needle 4 and the blood flow position are compared by the comparison section 184 and a needle stop signal is sent to the needle stop mechanism 193 of the biopsy needle insertion/retraction section 190 from the needle stop signal generating section 186, are the same as in the case of the construction described referring to the ultrasound diagnostic signal processing device 140 of FIG. 13.

(Effects)

With the sixth embodiment, just as in the case of the fifth embodiment shown in FIG. 13 and FIG. 14, the biopsy needle 4 is stopped when the position of the tip of the biopsy needle 4 and the blood flow position approach are within the approach/excursion distance, so biopsy can be conducted with confidence.

The ultrasound probe of the embodiments shown in FIG. 1 to FIG. 15 is not restricted to an ultrasound endoscope but could be combined with an ultrasound probe of the external type.

Having described the preferred embodiments of the invention referring to the accompanying drawings, it should be understood that the present invention is not limited to those precise embodiments, and various changes and modifications thereof could be made by one skilled in the art without departing from the spirit or scope of the invention as defined in the appended claims.

What is claimed is:

1. A device for examining a subject, comprising:

an image capture section capable of acquiring an image of a subject;

an insertion/retraction member having a desired positional relationship with the image capture section and capable of being freely inserted/retracted with respect to the subject;

an image generating section that generates an image comprising an image of the subject acquired by the image capture section and an image of the insertion/retraction member;

a boundary position superimposition section that superimposes an insertion/refraction boundary marker indicating the position of an insertion/retraction boundary of the insertion/retraction member in the image generated by the image generating section; and an insertion/retraction direction alteration section that alters the direction of insertion/retraction of the insertion/retraction member, wherein the insertion/retraction boundary marker comprises at least an insertion/retraction direction boundary marker indicating the boundary of the direction of insertion/retraction of the insertion/retraction member.

2. The device for examining a subject according to claim 1, wherein the image capture section acquires an image of the subject by sending ultrasound to the subject and receiving ultrasound therefrom.

3. The device for examining a subject according to claim 1, wherein the insertion/refraction boundary marker comprises an insertion/retraction amount marker that indicates the amount of insertion/retraction of the insertion/retraction member.

4. The device for examining a subject according to claim 1, wherein the boundary position superimposition section detects the insertion/retraction member by performing image processing and calculates a position of the insertion/retraction boundary marker.

5. A device for examining a subject, comprising:

an image capture section capable of acquiring an image of a subject;

a medical instrument whose relative position with respect to the image capture section is specified and that is capable of insertion/retraction action for performing a medical action on the subject;

an image generating section that generates an image comprising an image of the subject and an image of the medical instrument to be displayed on a display;

a marking section that marks an insertion/retraction boundary marker of the medical instrument on the display; and an insertion/retraction direction alteration section that alters the direction of insertion/retraction of the medical instrument, wherein the insertion/retraction boundary marker comprises an insertion/refraction direction boundary marker indicating the boundary of the direction of insertion/retraction of at least the medical instrument.

6. The device for examining a subject according to claim 5, wherein the image capture section acquires an image of the subject by sending ultrasound to the subject and receiving ultrasound therefrom.

7. The device for examining a subject according to claim 5, wherein the insertion/retraction boundary marker comprises at least an insertion/retraction amount marker that indicates the amount of insertion/retraction of the medical instrument.

8. The device for examining a subject according to claim 5, wherein the boundary position superimposition section detects the medical instrument by performing image processing and calculates a position of the insertion/retraction boundary marker.

9. A device for examining a subject, comprising:
   an image capture section capable of acquiring an image of a subject;
   a medical instrument that is capable of performing a medical action on the subject;
   a holder that holds the medical instrument so as to enable insertion/retraction operation thereof and that defines the relative position of the medical instrument and the image capture section;
   an image generating section that generates an image comprising an image of the subject and an image of the medical instrument to be displayed on a display; and
   a marking section that marks an insertion/retraction boundary marker of the medical instrument on the display; and
   an insertion/retraction direction alteration section that alters the direction of insertion/retraction of the medical instrument,
   wherein the insertion/retraction boundary marker comprises at least an insertion/retraction direction boundary marker indicating the boundary of the direction of insertion/retraction of the medical instrument.

10. The device for examining a subject according to claim 9, wherein the image capture section acquires an image of the subject by sending ultrasound to the subject and receiving ultrasound therefrom.

11. The device for examining a subject according to claim 9, wherein the insertion/retraction boundary marker comprises an insertion/retraction amount marker that indicates the amount of insertion/retraction of the medical instrument.

12. The device for examining a subject according to claim 9, wherein the boundary position superimposition section detects the medical instrument by performing image processing and calculates a position of the insertion/retraction boundary marker.

13. A device for examining a subject, comprising:
   an image capture section capable of acquiring an image of a subject;
   a medical instrument that is capable of insertion/retraction operation and that is capable of performing a medical action on the subject;
   an image generating section that generates an image comprising an image of the subject;
   an image of the medical instrument to be displayed on a display;
   a marking section that marks a region, which prohibits the medical instrument from being inserted into/retracted from, on the image;
   a calculating section that calculates the relative distance of the medical instrument and the region marked on the image;
   a stop provided on the medical instrument that prohibits the insertion/retraction action of the medical instrument in accordance with the results of the calculation by the calculating section; and
   an insertion/retraction direction alteration section that alters the direction of insertion/retraction of the medical instrument,
   wherein the region marked indicates a boundary of the direction of insertion/refraction of at least the medical instrument.

14. The device for examining a subject according to claim 13, wherein the image capture section acquires an image of the subject by sending ultrasound to the subject and receiving ultrasound therefrom.

15. The device for examining a subject according to claim 13, wherein the region that is marked on the image is a blood vessel region of the subject.

16. A method of examining a subject, comprising:
   displaying on a monitor an image obtained by the medical instrument;
   displaying on the monitor an image of an insertion/retraction member corresponding to an insertion/retraction member which has a desired positional relationship with the medical instrument and who can be freely inserted/retracted;
   calculating an insertion/retraction boundary position in accordance with the positional relationship of the medical instrument and the insertion/refraction member; and
   displaying on the monitor an insertion/refraction marker indicating the insertion/retraction boundary position of the insertion/retraction member; and
   altering the direction of insertion/retraction of the insertion/retraction member,
   wherein the insertion/retraction boundary marker comprises at least an insertion/retraction direction boundary marker indicating the boundary of the direction of insertion/retraction of the insertion/retraction member.

17. An ultrasound diagnostic device, comprising:
   an ultrasound diagnostic image capture section that obtains an ultrasound diagnostic image by performing transmission/reception of ultrasound signals with respect to a subject within a body cavity;
   an insertion section that is inserted into the body cavity;
   a biopsy needle that pierces the subject by insertion of the insertion section;
   superimposition means that superimposes a boundary of advancement of the piercing direction of the biopsy needle on the ultrasound diagnostic image; and
   an insertion direction alteration section that alters the direction of insertion/retraction of the insertion section,
   wherein the boundary superimposed by the superimposition means indicates a boundary of the direction of insertion/retraction of the insertion section.

18. An ultrasound diagnostic device, comprising:
   an ultrasound diagnostic image capture section that obtains an ultrasound diagnostic image by performing transmission/reception of ultrasound signals with respect to a subject within a body cavity;
   blood flow position detection means that detects the position of blood flow on the ultrasound diagnostic image;
   needle position detection means that detects the needle tip position of a biopsy needle on the ultrasound diagnostic image; and comparison means that compares the position of the needle tip from the needle position detection means with the blood flow position from the blood flow position detection means;

wherein, when the comparison means determines that the blood flow position and the needle tip position are within a prescribed distance, a stop signal is output to a biopsy needle insertion/retraction section having means for preventing further advance of the biopsy needle upon receipt of the stop signal.

* * * * *